(12) United States Patent
Omata et al.

(10) Patent No.: US 8,560,253 B2
(45) Date of Patent: Oct. 15, 2013

(54) MATERIAL HARDNESS DISTRIBUTION DISPLAY SYSTEM AND MATERIAL HARDNESS DISTRIBUTION DISPLAY METHOD

(75) Inventors: Sadao Omata, Tokyo (JP); Yoshinobu Murayama, Tokyo (JP)

(73) Assignee: Nihon University, Tokyo (JP)

( * ) Notice: Subject to any disclaimer, the term of this patent is extended or adjusted under 35 U.S.C. 154(b) by 355 days.

(21) Appl. No.: 13/127,827

(22) PCT Filed: Nov. 13, 2009

(86) PCT No.: PCT/JP2009/069318
§ 371 (c)(1),
(2), (4) Date: May 5, 2011

(87) PCT Pub. No.: WO2010/055904
PCT Pub. Date: May 20, 2010

(65) Prior Publication Data
US 2011/0213575 A1 Sep. 1, 2011

(30) Foreign Application Priority Data
Nov. 13, 2008 (JP) ................................. 2008-290629

(51) Int. Cl.
*G01M 3/00* (2006.01)
*G01N 29/00* (2006.01)
*G01B 5/02* (2006.01)
*G01B 5/06* (2006.01)

(52) U.S. Cl.
USPC ................................. 702/56; 702/33; 73/573

(58) Field of Classification Search
USPC ........................................ 702/33, 56; 73/573
See application file for complete search history.

(56) References Cited

U.S. PATENT DOCUMENTS

| | | |
|---|---|---|
| 5,766,137 A | 6/1998 | Omata |
| 6,854,331 B2 | 2/2005 | Omata |
| 2007/0083116 A1 | 4/2007 | Sato |

FOREIGN PATENT DOCUMENTS

| | | |
|---|---|---|
| JP | A-9-145691 | 6/1997 |
| JP | A-2002-272743 | 9/2002 |
| JP | A-2004-283547 | 10/2004 |
| JP | A-2007-82725 | 4/2007 |

OTHER PUBLICATIONS

International Search Report issued in International Application N. PCT/JP2009/069318 on Dec. 28, 2009 (with translation).

*Primary Examiner* — Janet Suglo
(74) *Attorney, Agent, or Firm* — Oliff & Berridge, PLC

(57) ABSTRACT

A material hardness distribution display system (10) includes a probe unit (20) in which a plurality of probe elements (22) are two-dimensionally arranged. Each of the probe elements (22) has an oscillator (26) for introducing oscillation into a biological tissue and an oscillation detection sensor (28) which detects a reflected wave. The probe elements (22) are successively selected by a switch circuit (50) and connected to a hardness calculation unit (70) and a measurement depth calculation unit (82). The hardness calculation unit (70) executes a frequency component analysis for an incident wave signal to the oscillator (26) and a reflected wave signal from the oscillation detection sensor (28) to calculate the hardness of the biological tissue on the basis of the analysis results. The measurement depth calculation unit (82) calculates a measurement depth inside the biological tissue at a position where the hardness has been measured, on the basis of a temporal position of the incident wave signal and a temporal position of the reflected wave signal. They are correlated to the respective probe elements (22).

8 Claims, 7 Drawing Sheets

MATERIAL HARDNESS DISTRIBUTION DISPLAY SYSTEM AND MATERIAL HARDNESS DISTRIBUTION DISPLAY METHOD

TECHNICAL FIELD

The present invention relates to a material hardness distribution display system and a material hardness distribution display method, and more particularly, it relates to a material hardness distribution display system which can display a relation between hardnesses of a living body and measurement depths at which the hardnesses have been measured, and a material hardness distribution display method.

BACKGROUND TECHNOLOGY

As a technology for evaluating a hardness of a material, a method using an ultrasonic wave is known. Furthermore, although a difference between hardnesses of the material causes a larger change to a phase of the ultrasonic wave than to a frequency thereof, the accuracy of phase measurement technology is not necessarily high, and in consideration of this the present inventors have contrived a technology which converts the phase change into a frequency change, and have disclosed the technology in Patent Document 1. This technology has a constitution including an oscillator which introduces the ultrasonic wave into the material; an oscillation detection sensor which detects a reflected wave from the material; an amplifier having an input end connected to a signal output end of the oscillation detection sensor; a phase shift circuit disposed between the output end of the amplifier and a signal input end of the oscillator to change the frequency, thereby shifting a phase difference to zero, when the phase difference is generated between an input waveform to the oscillator and an output waveform from the oscillation detection sensor; and a frequency change amount detection means for detecting a frequency change amount for shifting the phase difference to zero. In this constitution, the frequency change amount detection means shifts the phase difference due to the hardness difference to zero, thereby converting the phase difference into a frequency change amount. This conversion uses a previously obtained reference transmission function indicating a relation between an amplitude gain and a phase of the reflected wave with respect to the frequency.

Moreover, as a device contributing to the development of this technology, Patent Document 2 discloses a material property measuring device which includes a sensor comprising pulse introducing means and pulse receiving means. The measuring device analyzes frequencies of an incident wave and a reflected wave thereof, compares a spectral distribution of the incident wave with that of the reflected wave to specify a phase difference θx which is a difference between a phase of the incident wave and a phase of the reflected wave at each frequency fx, and inputs the fx and θx to perform calculation by use of a previously obtained reference transmission characteristic curve, thereby obtaining a hardness of the material from a change df of the frequency when the input θx is set to zero.

Furthermore, Patent Document 3 discloses a device for detecting a hard spot of a living body to which the technologies of Patent Documents 1 and 2 are applied, and the device includes a plurality of probe elements each having an oscillator which introduces oscillation into a biological tissue and an oscillation detection sensor which detects a reflected wave. The probe elements are successively selected by a hardness calculation switch circuit and connected to a hardness calculation unit. It is also disclosed therein that the probe elements are provided with corresponding pressure sensors, respectively, and hardness data of the probe elements at pressing pressures in a predetermined range are two-dimensionally displayed on a display unit to detect a hard spot.

In addition, as a device by inventors other than the present inventor, Patent Document 4 discloses an ultrasonic diagnosis device including an ultrasonic probe provided with an ultrasonic transducer which irradiates a part of a subject to be observed with an ultrasonic wave, and receives an echo signal from the part of the subject to be observed, whereby an ultrasonic image is generated from sound line data obtained by digitizing the echo signal, and it is then displayed. The ultrasonic diagnosis device uses a timing signal synchronized with two points in one cycle of an electrocardiographic signal on the basis of movement of the heart of the subject to acquire sound line data for two frames at the two points, calculates strain of a biological tissue from the sound line data for the two frames having a time difference, and displays an elastic image quantitatively indicating a hardness on the basis of the strain.

PRIOR ART DOCUMENTS

Patent Documents

Patent Document 1: JP-A-9-145691
Patent Document 2: JP-A-2002-272743
Patent Document 3: JP-A-2004-283547
Patent Document 4: JP-A-2007-82725

DISCLOSURE OF THE INVENTION

As described above, according to the technology of Patent Document 3 to which Patent Documents 1 and 2 are applied, a two-dimensional distribution of the hardness of a material can be accurately obtained. However, a three-dimensional distribution of the hardness of the material cannot be obtained with only the technologies of Patent Documents 1, 2 and 3. On the other hand, Patent Document 4 discloses that an elastic image indicating the hardness of the heart is displayed by using an ultrasonic technology together with an electrocardiographic technology. Therefore, when the technology of Patent Document 4 is used, it is possible to obtain the three-dimensional distribution of the hardness of the heart. However, the technology of Patent Document 4 uses the electrocardiographic technology, and hence it is impossible to obtain the three-dimensional distribution of the hardness of a general material.

An object of the present invention is to provide a material hardness distribution display system which can associate the hardness of a material with a depth where the hardness has been measured, by a comparatively simple constitution, and a material hardness distribution display method. Another object is to provide a material hardness distribution display system which can obtain a three-dimensional distribution of the hardness of a material by a comparatively simple constitution, and a material hardness distribution display method.

A material hardness distribution display system according to the present invention is characterized by including an oscillator which introduces a pulse wave into a material to be measured; an oscillation detection sensor which receives a reflected wave when the introduced pulse wave is reflected from the material to be measured; incident wave frequency component analysis means for executing a frequency analysis which breaks down the incident wave into a plurality of sine wave components and cosine wave components to obtain a spectral distribution of a frequency of each of the sine wave components and a phase obtained from the sine wave component and the cosine wave component at the frequency; reflected wave frequency component analysis means for executing a frequency analysis which breaks down the reflected wave into a plurality of sine wave components and cosine wave components to obtain a spectral distribution of a frequency of each of the sine wave components and a phase obtained from the sine wave component and the cosine wave component at the frequency; frequency phase difference calculation means for comparing the spectral distribution of the incident wave with the spectral distribution of the reflected wave, and calculating, with respect to each of the frequencies fx constituting the distributions, a phase difference θx which is a difference between the phase of the incident wave and the phase of the reflected wave at the frequency fx; hardness calculation means for calculating the hardness of the material to be measured, on the basis of data of a set of the frequency fx and the phase difference θx; measurement depth calculation means for calculating a measurement depth which is a depth at a position where the hardness has been measured, on the basis of a time of introducing the incident wave and a time of receiving the reflected wave used for the calculation of the hardness; and display means for correlating and displaying the hardness and the measurement depth.

Moreover, preferably in the material hardness distribution display system according to the present invention, the probe elements each including a set of the oscillator and the oscillation detection sensor are two-dimensionally arranged; the hardness calculation means calculates the hardnesses at positions of the probe elements, respectively, on the basis of the incident waves and the reflected waves by the two-dimensionally arranged probe elements, to obtain a two-dimensional distribution of the hardness; the measurement depth calculation means calculates measurement depths at the positions of the probe elements, respectively, on the basis of the incident waves and the reflected waves by the two-dimensionally arranged probe elements, to obtain a two-dimensional distribution of the measurement depth; and the display means correlates the two-dimensional distribution of the hardness and the two-dimensional distribution of the measurement depth with respect to the material to be measured, to display a three-dimensional hardness distribution.

Furthermore, the material hardness distribution display system according to the present invention further comprises storage means for correlating two-dimensional coordinate positions of the probe elements with identification addresses of the probe elements when the probe elements are two-dimensionally arranged and storing the positions; the hardness calculation means obtains hardnesses at the positions of the probe elements correlated with the identification addresses of the probe elements; the measurement depth calculation means obtains measurement depths at the positions of the probe elements correlated with the identification addresses of the probe elements; a reading means reads from the storage means the two-dimensional coordinate position corresponding to the identification address of each of the probe elements; the display means includes measurement depth two-dimensional display means for displaying the distribution of the measurement depth in a two-dimensional coordinate system by use of the measurement depth corresponding to the identification address, and hardness two-dimensional display means for displaying the distribution of the hardness in the two-dimensional coordinate system by use of the hardness at the position of the probe element corresponding to the read identification address; and the display means preferably superimposes the distribution of the hardness in the two-dimensional coordinate system on the distribution of the measurement depth in the same two-dimensional coordinate system, to display the three-dimensional hardness distribution.

Additionally, in the material hardness distribution display system according to the present invention, the hardness calculation means preferably includes storage means for storing a previously obtained reference transmission function indicating a relation between an amplitude gain and a phase of the reflected wave with respect to the frequency of the incident wave when the oscillation having an arbitrary frequency is introduced; a frequency change amount detection unit which inputs the frequency fx and the phase difference θx to obtain df which is a change from the frequency fx when the phase difference θx is set to zero, by use of the reference transmission function; and hardness conversion means for converting df obtained by the frequency change amount detection unit into the hardness, on the basis of previously obtained hardness-df characteristics.

Moreover, in the material hardness distribution display system according to the present invention, the hardness calculation means preferably calculates the hardness of the material to be measured on the basis of a set of a maximum phase difference θx(MAX) and a frequency fx(MAX) corresponding to the maximum phase difference.

Furthermore, a material hardness distribution display method according to the present invention preferably includes an incident wave frequency component analysis step of executing a frequency analysis which breaks down an incident wave introduced as a pulse into a material to be measured by an oscillator into a plurality of sine wave components and cosine wave components, to obtain a spectral distribution of a frequency of each of the sine wave components and a phase obtained from the sine wave component and the cosine wave component at the frequency; a reflected wave frequency component analysis step of executing a frequency analysis which breaks down a reflected wave from the material to be measured which is detected by an oscillation detection sensor, into a plurality of sine wave components and cosine wave components, to obtain a spectral distribution of a frequency of each of the sine wave components and a phase obtained from the sine wave component and the cosine wave component at the frequency; a frequency phase difference calculation step of comparing the spectral distribution of the incident wave with the spectral distribution of the reflected wave to calculate, with respect to each of frequencies fx constituting the distributions, a phase difference θx which is a difference between the phase of the incident wave and the phase of the reflected wave at the frequency fx; a hardness calculation step of calculating the hardness of the material to be measured on the basis of data of a set of the frequency fx and the phase difference θx; a measurement depth calculation step of calculating a measurement depth which is a depth at a position where the hardness has been measured, on the basis of a time of introducing the incident wave and a time of receiving the reflected wave used for the calculation of the hardness; and a display step of correlating and displaying the hardness and the depth.

Additionally, preferably in the material hardness distribution display method according to the present invention, probe elements each including a set of the oscillator and the oscillation detection sensor are two-dimensionally arranged; the hardness calculation step calculates the hardnesses at positions of the probe elements, respectively, on the basis of the incident waves and the reflected waves by the two-dimensionally arranged probe elements, to obtain a two-dimensional distribution of the hardness; the measurement depth calculation step calculates measurement depths at the positions of the probe elements, respectively, on the basis of the incident waves and the reflected waves by the two-dimensionally arranged probe elements, to obtain a two-dimensional distribution of the measurement depth; and the display step correlates the two-dimensional distribution of the hardness and the two-dimensional distribution of the measurement depth with respect to the material to be measured, to display a three-dimensional hardness distribution.

Moreover, the material hardness distribution display method according to the present invention preferably uses a storage device which correlates two-dimensional coordinate positions of the probe elements with identification addresses of the probe elements when the probe elements are two-dimensionally arranged and which stores the positions; the hardness calculation step obtains hardnesses at the positions of the probe elements correlated with the identification addresses of the probe elements; the measurement depth calculation step obtains measurement depths at the positions of the probe elements correlated with the identification addresses of the probe elements; a reading step reads from the storage device, the two-dimensional coordinate position corresponding to the identification address of each of the probe elements; the display step includes a measurement depth two-dimensional display step of displaying the distribution of the measurement depth in a two-dimensional coordinate system by use of the measurement depth corresponding to the identification address, and a hardness two-dimensional display step of displaying the distribution of the hardness in the two-dimensional coordinate system by use of the hardness at the position of the probe element corresponding to the read identification address; and the display step superimposes the distribution of the hardness in the two-dimensional coordinate system on the distribution of the measurement depth in the same two-dimensional coordinate system, to display the three-dimensional hardness distribution.

According to the above constitution, a material hardness distribution display system introduces a pulse wave into a material to be measured, receives a reflected wave reflected from the material, executes a frequency analysis of the incident wave and the reflected wave, and calculates the hardness of the material to be measured on the basis of the result. This technology is an application of the disclosure of Patent Document 2. Then, on the basis of a time of introducing the incident wave and a time of receiving the reflected wave which are used for the calculation of the hardness, the system calculates a measurement depth which is a depth at a position where the hardness has been measured, and correlates and displays the hardness and the measurement depth. In this way, a comparatively simple constitution makes it possible to associate the hardness of the material with the measurement depth where the hardness has been measured, to display the association.

Moreover, in the material hardness distribution display system, pulse transmission/reception means including a set of pulse introducing means and pulse receiving means are two-dimensionally arranged, and hence a two-dimensional distribution of the hardness can be obtained. Then, on the basis of the incident waves and the reflected waves created and received by the two-dimensionally arranged pulse transmission/reception means, a two-dimensional distribution of the depth at the position where the hardness has been measured can be calculated, and this distribution is displayed in combination with the two-dimensional distribution of the hardness, which makes it possible to display a three-dimensional distribution of the hardness.

Furthermore, the material hardness distribution display system correlates two-dimensional coordinate positions of probe elements with identification addresses of the probe elements when the probe elements are two-dimensionally arranged, to store the positions, obtains the hardnesses at positions of the probe elements correlated with the identification addresses of the probe elements, obtains measurement depths at the positions of the probe elements correlated with the identification addresses of the probe elements, reads, from the storage means, the two-dimensional coordinate position corresponding to the identification address of each probe element, displays a distribution of the measurement depth in a two-dimensional coordinate system by use of the measurement depth corresponding to the identification address, displays a distribution of the hardness in the two-dimensional coordinate system by use of the hardness at the position of the probe element corresponding to the read identification address, and superimposes the distribution of the hardness in the two-dimensional coordinate system on the distribution of the measurement depth in the two-dimensional coordinate system, to display the three-dimensional hardness distribution. In this way, the correlation is executed by using the identification addresses of the probe elements, and hence the accurate three-dimensional distribution of the hardness is possible.

Moreover, in the material hardness distribution display system, hardness calculation means stores a previously obtained reference transmission function indicating a relation between an amplitude gain and a phase of the reflected wave with respect to the frequency of the incident wave when the oscillation having an arbitrary frequency is introduced. The means includes a frequency change amount detection unit which inputs a frequency fx and a phase difference θx to obtain df which is a change from the frequency fx when the phase difference θx is set to zero. Then, the means converts df obtained by the frequency change amount detection unit to the hardness, on the basis of previously obtained hardness-df characteristics. This technology is an application of the disclosure of Patent Document 2. Therefore, the hardness and the depth can be accurately associated and displayed by use of an already successfully achieved technology.

Furthermore, the material hardness distribution display system calculates the hardness of the material to be measured on the basis of a set of a maximum phase difference θx(MAX) and a frequency fx(MAX) at the maximum phase difference. The fx(MAX) and θx(MAX) can be regarded as typical characteristics, and hence the calculated hardness can be used as a typical value.

BEST MODE FOR CARRYING OUT THE INVENTION

Figure 1:
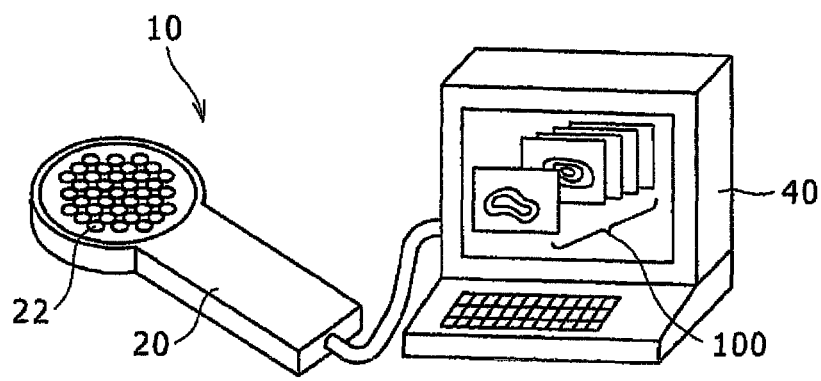
FIG. 1 is a diagram showing a constitution of a material hardness distribution display system in an embodiment according to the present invention.

Hereinafter, an embodiment according to the present invention will be described in detail with reference to the drawings. Hereinafter, as a material to be measured, a biological tissue, especially an abnormal part having a different hardness inside a living body will be described, but the material may be a general material other than the biological tissue. A material, a shape, and a dimension described hereinafter are exemplary, and they may be appropriately changed in accordance with purpose of use Hereinafter, similar elements in all the drawings will be denoted with the same reference numerals, and redundant description will be omitted. Moreover, in the present description, previously used reference numerals will be employed if necessary.

FIG. 1 is a diagram showing a constitution of a material hardness distribution display system 10. The material hardness distribution display system 10 includes a probe unit 20 in which a plurality of probe elements 22 are two-dimensionally arranged, and a controller 40 which is connected to the probe unit 20 to accomplish three-dimensional display 100 of a hardness on the basis of measured data.

The probe unit 20 includes a disc-like probe base section and a grip section which extends from the probe base section and can be held by a hand, and in the probe base section, a plurality of probe elements 22 which are pressed on the surface of the living body are two-dimensionally arranged. In an example of FIG. 1, a total of 37 probe elements 22 are two-dimensionally arranged. Needless to say, the number of the probe elements 22 is not limited, as long as the two-dimensional arrangement is appropriately accomplished.

Different address numbers are assigned as identification addresses to the respective probe elements 22. At the individual identification addresses, coordinate position values are obtained with respect to a two-dimensional coordinate system preset to the probe unit 20, and stored in an appropriate memory of the controller 40. In the two-dimensional coordinate system, for example, a direction which is parallel to a center line extending from the probe base section to the grip section is a Y-axis, a direction which is orthogonal to the above direction is an X-axis, an XX-plane constituted of both the axes is a plane of the probe base section where the probe elements 22 are arranged, and an appropriate position of the probe base section can be regarded as an origin of the XY-plane. The position of the origin is preferably marked beforehand. For example, when a specific one of the probe elements 22 is regarded as the position of the origin, a special color can be assigned to the probe element 22.

In an example of a size of the probe base section, a diameter is about 60 mm and a thickness is about 20 mm. In an example of a size of the grip section, in conformity to the probe base section, a thickness is about 20 mm, a handle portion width is about 45 mm, and a length is about 100 mm. As the probe unit 20, an appropriately formed plastic article can be used except for the probe elements 22.

Figure 2:
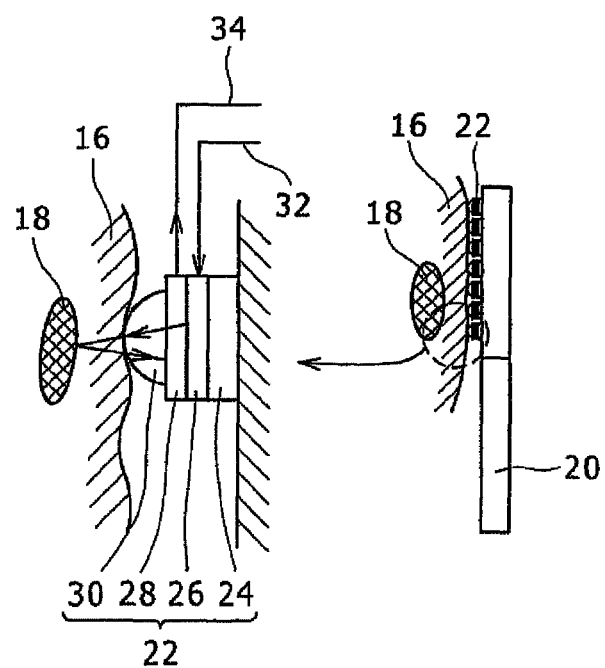
FIG. 2 is an explanatory view of a state where a probe unit is pressed against a biological tissue in the embodiment according to the present invention.

FIG. 2 is an explanatory view of a state where the probe unit 20 is pressed against a biological tissue 16 as the material to be measured. Here, it is presumed that a hard spot 18 is present as an abnormal part having different hardness inside the biological tissue 16. As shown in FIG. 2, the plurality of probe elements 22 of the probe unit 20 are appropriately pressed against the biological tissue 16, whereby a region of two-dimensional spread of the probe base section can be measured in a state where they are pressed without moving the probe base section.

FIG. 2 further shows an enlarged view of the state where the one probe element 22 is pressed against the biological tissue 16. The probe element 22 is an element having a function of introducing oscillation into the biological tissue 16 to detect a reflected wave from the biological tissue 16. When an incident wave and a reflected wave reciprocate through portions having the same elastic characteristics, responses to the elastic characteristics of the portions through which the waves reciprocate are cancelled. However, when the oscillation is introduced into a part of the biological tissue 16 having different elastic characteristics, i.e., the hard spot 18 of FIG. 2, only the response to reflection from the hard spot is detected.

In view of the above fact, when pressed against the biological tissue 16, the probe element 22 operates as an element having a function of introducing the oscillation into the hard spot 18 which is the abnormal part inside the biological tissue 16 to detect the reflected wave from the hard spot. It is to be noted that when the probe element 22 does not come in contact with the biological tissue 16, an air space between the element and the biological tissue 16 becomes the portion for the reciprocation having the same elastic characteristics. Therefore, when introducing the oscillation into the biological tissue 16 itself, the probe element 22 functions to detect the reflected wave from the biological tissue 16.

The probe element 22 has a structure in which a base portion 24, an oscillator 26, an oscillation detection sensor 28 and a contact ball 30 are laminated. The base portion 24 is a base for attaching each probe element 22 to the probe base section of the probe unit 20, and as the base portion 24, a disc having an appropriate size can be used. For example, a plastic disc having a diameter of 10 mm and a thickness of about several millimeters can be used. The contact ball 30 is made of a plastic resin such as a nylon resin and has a semispherical surface which functions to smoothly come in contact with the biological tissue under pressure. A semispherical radius of the contact ball 30 to be used is, for example, about 5 mm.

As the oscillator 26 and the oscillation detection sensor 28, for example, piezoelectric elements are used. When an alternating current signal is applied to the oscillator 26 and the oscillation detection sensor 28, the oscillator 26 exerts an electric energy-mechanical energy converting function to cause mechanical oscillation at the frequency of the alternating current signal, and the oscillation detection sensor 28 exerts a mechanical energy-electric energy converting function to cause the alternating current signal at the frequency of the oscillation by the application of the oscillation. Specifically, as the oscillator 26 and the oscillation detection sensor 28, there can be used, respectively, discs of the piezoelectric elements made of PZT or the like and provided with electrodes.

When the oscillator 26 and the oscillation detection sensor 28 are laminated, two piezoelectric elements are connected in series, and a connection point is grounded. One of the piezoelectric elements can be used as the oscillator 26, and the other piezoelectric element can be used as the oscillation detection sensor 28. In FIG. 2, a ground which is this common contact point is omitted. The oscillator 26 is connected to a signal line 32, and as will be described later, a pulse driving signal is supplied to the oscillator from a pulse wave generator 60 of the controller 40. In consequence, the oscillator 26 generates an ultrasonic incident wave, and the generated wave is then introduced into the biological tissue 16. The oscillation detection sensor 28 detects the reflected wave from the biological tissue 16, and outputs, as a reflected wave signal, to a signal line 34. The signal lines 32 and 34 pass through the probe base section and the grip section, and are connected to the controller 40 via an appropriate cable.

Figure 3:
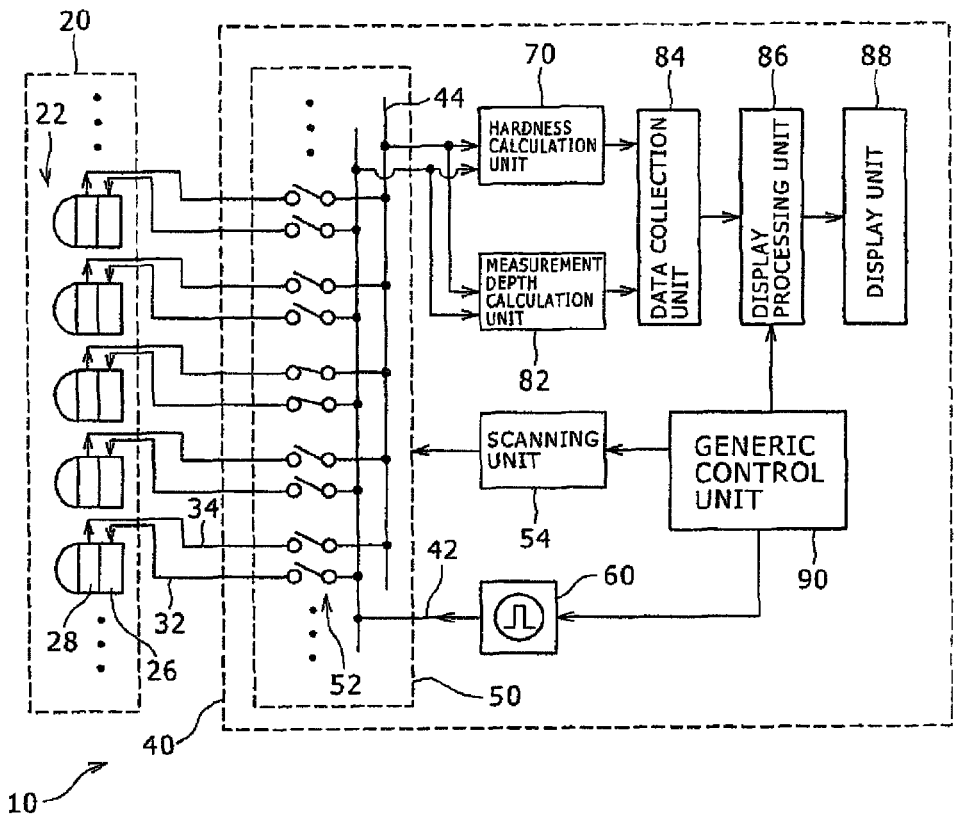
FIG. 3 is a block diagram showing a flow of a signal of a material hardness distribution display system in the embodiment according to the present invention.

FIG. 3 is a block diagram showing a flow of a signal of the material hardness distribution display system 10. The material hardness distribution display system 10 includes the probe unit 20 and the controller 40 as described above, and these components are connected to each other via the signal lines 32 and 34 for each of the probe elements 22.

The controller 40 includes a switch circuit 50, a scanning unit 54 which operates the switch circuit 50 to successively select the plurality of probe elements 22 of the probe unit 20, a pulse wave generator 60 which supplies a driving signal to the oscillator 26 of the probe element 22 selected via the switch circuit 50, a hardness calculation unit 70 which calculates the hardness of the hard spot 18 on the basis of an incident wave signal and a reflected wave signal with respect to the one probe element 22 selected via the switch circuit 50, and a measurement depth calculation unit 82 which calculates the depth of a portion where the hardness has been calculated.

Moreover, the controller 40 includes a data collection unit 84 which collects and stores data calculated from the hardness calculation unit 70 and data calculated from the measurement depth calculation unit 82; a display processing unit 86 which performs display processing such as coordinate conversion processing so as to associate a two-dimensional distribution of the hardness with a two-dimensional distribution of the depth, thereby three-dimensionally displaying the distributions, on the basis of the collected data; a display unit 88 which displays the three-dimensional display 100 of the hardness; and a generic control unit 90 which generically controls the whole operation of the elements constituting the controller 40.

The controller 40 can be constituted by an appropriate computer, and functions of the above constituent elements, excluding the pulse wave generator 60 and the switch circuit 50, can be realized by software, and can specifically be realized by executing a material hardness distribution display program. Needless to say, some of the functions realized by the software may be realized by hardware.

The switch circuit 50 is a selection switch circuit having a function of selecting the probe element 22 connected to the pulse wave generator 60, the hardness calculation unit 70 and the measurement depth calculation unit 82. That is, the switch circuit has a function of successively switching the signal lines 32 from the oscillators 26 and the signal lines 34 from the oscillation detection sensors 28 using a plurality of switches 52, to connect the pulse wave generator 60 to the signal lines 32, and to connect the hardness calculation unit 70 and the measurement depth calculation unit 82 to the signal lines 34 and 32. To facilitate the above successive switching, the probe elements 22 are provided with probe element addresses.

As the pulse wave generator 60, a commercially available pulse wave generator can be used. When a primary characteristic frequency of the oscillator 26 is 1 MHz, a pulse width of a pulse wave which is about several times as much as 1/(400 kHz) is preferably used. Alternatively, a rectangular pulse on which 400 KHz is superimposed may be used.

An output of the pulse wave generator 60 is connected to a signal line 42. The signal line 42 is connected to an input terminal of each of the oscillators 26 via the switch circuit 50. That is, the pulse wave from the pulse wave generator 60 is introduced into the biological tissue 16 from each of the oscillators 26 in accordance with successive selection of each of the probe elements 22 by the switch circuit 50, and simultaneously, as shown in FIG. 3, the pulse wave is input into the hardness calculation unit 70 and the measurement depth calculation unit 82. It is to be noted that the reflected wave from the biological tissue 16 is detected by each of the oscillation detection sensors 28, and input into the hardness calculation unit 70 and the measurement depth calculation unit 82 via a signal line 44 by the switch circuit 50. In this way, the pulse wave introduced into the biological tissue 16 and the reflected wave from the inside of the biological tissue 16 are input into the hardness calculation unit 70 and the measurement depth calculation unit 82.

On an output side of the pulse wave generator 60, a gate circuit which regulates the output of the pulse wave or the like is provided, and one pulse wave is preferably output in conjunction with the switching by the switch circuit 50. Moreover, a repeating frequency of the pulse wave output from the pulse wave generator 60 is set to be the same as a switching frequency of the switch circuit 50, whereby the gate circuit or the like can be omitted.

For each of the probe elements 22 selected by the switch circuit 50, the hardness calculation unit 70 is a circuit for calculating the hardness of the hard spot 18 which is an abnormal part inside the biological tissue 16 brought into contact with the probe element 22, on the basis of signals at signal input ends of the oscillators 26, i.e., the signals of the signal lines 32 or the signal line 42, and signals at signal output ends of the oscillation detection sensors 28, i.e., the signals of the signal lines 34 or the signal line 44.

Calculated hardness data are correlated with the respective probe elements 22, and transmitted to the data collection unit 84. During the correlating, for example, the above probe element addresses can be used. An internal constitution of the hardness calculation unit 70 will be described later in detail.

For each of the probe elements 22 selected by the switch circuit 50, the measurement depth calculation unit 82 is a circuit for calculating the measurement depth which is a depth at a position where the hardness calculation unit 70 has measured the hardness, on the basis of the signals at the signal input ends of the oscillators 26, i.e., the signals of the signal lines 32 or the signal line 42, and signals at the signal output ends of the oscillation detection sensors 28, i.e., the signals of the signal lines 34 or the signal line 44. The position where the hardness calculation unit 70 has measured the hardness is the hard spot 18, which is the abnormal part inside the biological tissue 16 brought into contact with the probe element 22, and hence the measurement depth calculation unit 82 and the hardness calculation unit 70 simultaneously calculate the measurement depth and the hardness at the same position.

Measurement depth data is calculated with a distance from the probe element 22, and an outer dimension of the probe element 22 is known beforehand, whereby this dimension can be converted to the depth data from the position where the probe element 22 comes in contact with the biological tissue 16. Here, it is considered that the measurement depth data indicates the distance from the surface of the biological tissue 16, thereby continuing the description. The calculated measurement depth data is correlated with the respective probe elements 22, and transmitted to the data collection unit 84. During the correlating, as described above, the probe element addresses can be used. Contents of measurement depth calculation will be described later in detail.

The data collection unit 84 is a storage device which correlates and stores the hardness data and the measurement depth data for each of the probe elements 22. During the correlating, the above probe element addresses are used, and the hardness data and the measurement depth data can be arranged and stored for each of the probe element addresses.

The display processing unit 86 is a circuit which reads necessary data from the data collection unit 84, and performs signal processing to three-dimensionally display the hardness. Specifically, the data is organized as two-dimensional data of the hardness at the same measurement depth, on the basis of the two-dimensional distribution data of the hardness and the two-dimensional data of the measurement depth. When the data is not necessarily the hardness data at the same measurement depth, but is the hardness data at a measurement depth before and after the same measurement depth, interpolation or extrapolation is performed, whereby the hardness data at the measurement depth may be obtained. In this way, the hardness data at the respective measurement depths is organized, for example, at preset intervals of the measurement depth, and hence the data is processed suitably for display of an image.

For example, processing to display the hardness distribution along a reference coordinate system is performed. In consequence, the data can be processed suitably for the display of a shape of the hard spot 18. For example, the processing can be performed to obtain contour display of the hardness, color display corresponding to the hardness, or shading display of color corresponding to the hardness. In consequence, the processing can be performed suitably for the display of the degree of abnormality in the hard spot 18. Moreover, two-dimensional data of the hardness for each depth is collected, whereby three-dimensional display of the hardness at a three-dimensional coordinate can be obtained. In consequence, the data can be processed suitably for the three-dimensional display of an outer shape of the hard spot 18 and the three-dimensional display of the position of the abnormal part. Moreover, adequate statistical processing or the like is performed, whereby an average value of the hardness, a hardness distribution graph or the like may be displayed.

The data subjected to the display processing is output to the display unit 88. The display unit 88 is a display of the controller 40, a printer connected to this controller or the like. FIG. 1 shows the three-dimensional display 100 of the hardness is performed as a set of the two-dimensional hardness distribution for each measurement depth. Moreover, the controller 40 is provided with an interface which transmits a signal to the outside, and the data subjected to the display processing is output to an external diagnosis device or the like, whereby further analysis may be advanced in detail.

Figure 4:
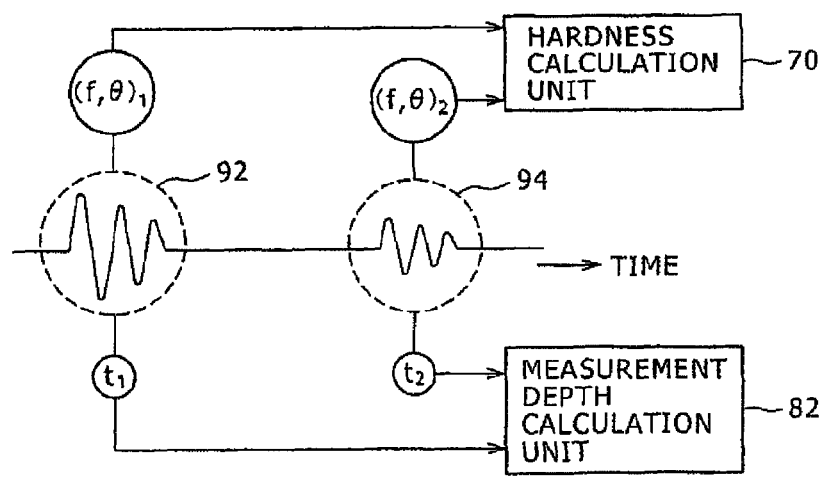
FIG. 4 is an explanatory view of obtaining hardness and measurement depth by use of the same incident wave signal and the same reflected wave signal in the embodiment according to the present invention.

As described above, data of the incident wave and data of the reflected wave in the respective probe elements 22 are input into both the hardness calculation unit 70 and the measurement depth calculation unit 82. That is, the same data is used to calculate the hardness on one hand and calculate the measurement depth on the other hand. This will be described with reference to FIG. 4. FIG. 4 shows that an incident wave signal 92 input into the probe element 22 and a reflected wave signal 94 obtained by reflecting the incident wave signal 92 from the inside of the biological tissue 16 in a case where the abscissa indicates time and the ordinate indicates a voltage which is a size of the signal. The incident wave signal 92 is introduced as a pulse wave. Therefore, when the next pulse wave is not introduced until the reflected wave arrives, the incident wave signal 92 and the reflected wave signal 94 can be accurately correlated.

The hardness calculation unit 70 executes a frequency analysis of a frequency f and a phase θ for the incident wave signal 92 and the reflected wave signal 94, respectively, and calculates the hardness of the hard spot 18 into which the incident wave is introduced and from which the reflected wave is returned, on the basis of the result. In FIG. 4, the state of the waveform of the incident wave signal 92 is (f, θ)1, and the state of the waveform of the reflected wave signal 94 is (f, θ)2. The hardness calculation unit 70 calculates the hardness of the hard spot 18 based on these states (f, θ)1 and (f, θ)2.

The measurement depth calculation unit 82 obtains temporal positions of the pulses of the incident wave signal 92 and the reflected wave signal 94, respectively, and calculates the measurement depth of the hard spot 18 from a difference between the temporal positions. In FIG. 4, the temporal position of the incident wave signal 92 is t1, and the temporal position of the reflected wave signal 94 is t2. The measurement depth calculation unit 82 calculates the measurement depth of the hard spot 18 on the basis of the temporal positions t1 and t2.

Figure 5:
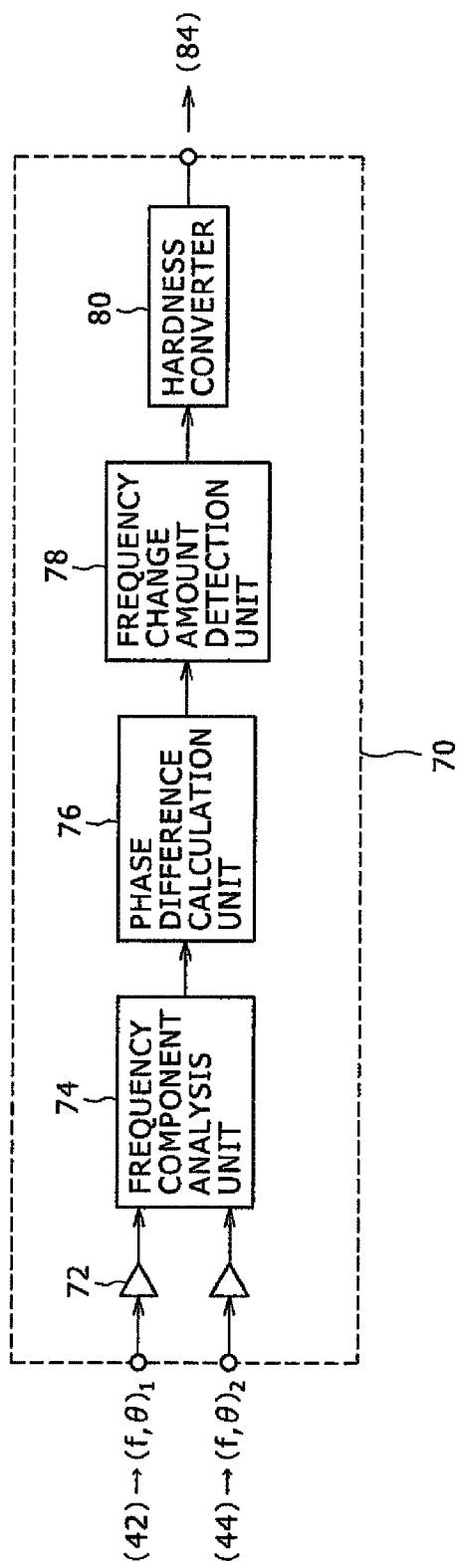
FIG. 5 is a block diagram of a hardness calculation unit in the embodiment according to the present invention.

Next, the hardness calculation unit 70 will be described in detail. FIG. 5 is a block diagram of the hardness calculation unit 70. The hardness calculation unit 70 is provided with the incident wave signal 92 from the signal line 42 and the reflected wave signal 94 from the signal line 44 as input data. These signals are amplified to appropriate signal levels by amplifiers 72, and respectively input into a frequency component analysis unit 74.

The frequency component analysis unit 74 executes a frequency component analysis of the incident wave and the reflected wave, breaks down the incident wave and the reflected wave into a plurality of sine wave components and cosine wave components, and obtains a relation between the frequency of each sine wave component and the phase determined by a ratio of the sine wave components with respect to the cosine wave components at the frequency. This relation between the frequency and the phase at the frequency is a so-called phase spectral distribution with respect to the frequency. Therefore, the frequency component analysis unit 74 has a function of obtaining the phase spectral distribution with respect to the frequency of the incident wave signal 92 and the phase spectral distribution with respect to the frequency of the reflected wave signal 94. The frequency analysis can use a technique usually referred to as Fourier analysis.

Figure 6A:
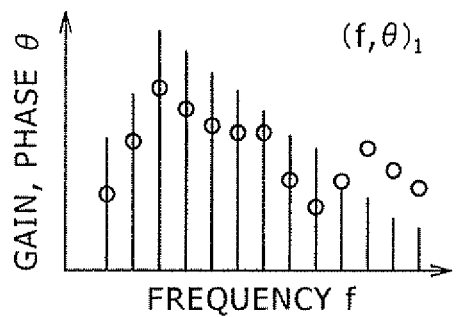
FIG. 6 is a diagram showing an example of phase spectral distributions with respect to frequencies of the incident wave signal and the reflected wave signal obtained by executing a frequency component analysis in the embodiment according to the present invention.
Figure 6B:
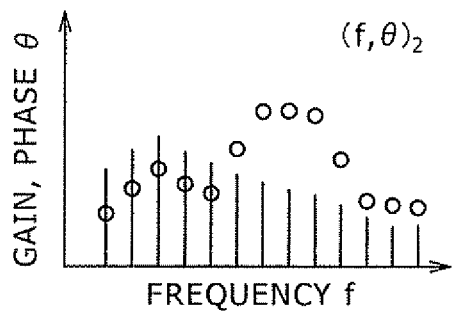

FIG. 6 shows an example of the phase spectral distribution with respect to the frequencies of the incident wave signal 92 and reflected wave signal 94, obtained by executing the frequency component analysis. FIG. 6(a) is the distribution with respect to the incident wave signal 92, and FIG. 6(b) is the distribution with respect to the reflected wave signal 94. In these diagrams, the abscissa indicates the frequency f, and the ordinate indicates a gain or the phase θ. Gain data is indicated by a length of a line segment, and data of the phase θ is indicated by circle marks. In FIGS. 6(a) and (b), origin points of the frequencies of the abscissas are aligned. In this way, the phase of the incident wave signal 92 and the phase of the reflected wave signal 94 indicate different values at the same frequency. This value difference reflects the hardness of the hard spot 18. The phase spectral distributions with respect to the frequencies of the incident wave signal 92 and the reflected wave signal 94 obtained in this manner are input into a phase difference calculation unit 76.

The phase difference calculation unit 76 has a function of comparing the phase spectral distribution of the incident wave signal 92 with the phase spectral distribution of the reflected wave signal 94, and calculating a phase difference θx which is a difference between the phase of the incident wave signal 92 and the phase of the reflected wave signal 94 with the respective frequencies fx, as the change of the frequency component between the incident wave signal 92 and the reflected wave signal 94.

Figure 7:
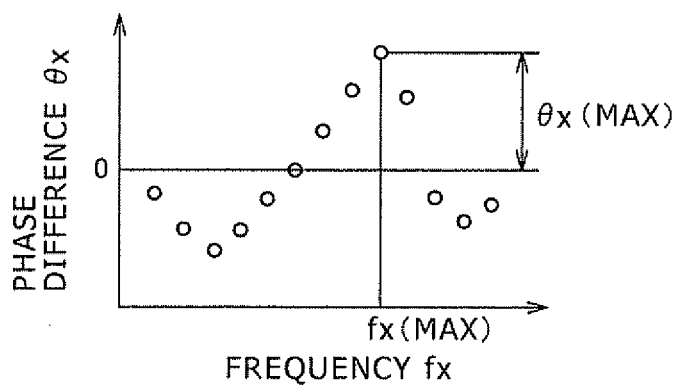
FIG. 7 is a diagram showing how to obtain a phase difference θx in the embodiment according to the present invention.

FIG. 7 shows how to obtain the phase difference θx. FIG. 7 shows data of the phase spectral distribution of the incident wave signal 92 and the phase spectral distribution of the reflected wave signal 94 obtained as shown in FIG. 6 in a case where the abscissa indicates the frequency fx and the ordinate indicates the phase difference θx which is a phase difference (θ2−θ1) as a difference between a phase θ2 of the reflected wave signal 94 and a phase θ1 of the incident wave signal 92 at the same frequency. In this case, the set itself of a plurality of pairs of fx and θx can be used to indicate the change of the frequency component between the incident wave signal 92 and the reflected wave signal 94. However, as an index which can easily be seen, a set of a frequency fx(MAX) at which the phase difference θx has a maximum value θx(MAX) and the value θx(MAX) can be used to typically indicate, as the hardness of the hard spot 18, the change of the frequency component between the incident wave signal 92 and the reflected wave signal 94. Hereinafter, these fx(MAX) and θx(MAX) will be used.

The obtained data of the frequency fx(MAX) and the phase difference θx(MAX) is input into a frequency change amount detection unit 78. The frequency change amount detection unit 78 has a function of calculating a frequency change amount df for changing the frequency to shift the phase difference θx(MAX) to zero with respect to the phase difference θx(MAX) at the frequency fx(MAX), by use of a reference transmission characteristic curve indicating a relation between an amplitude gain and a phase difference of the reflected wave signal 94 with respect to the frequency of the incident wave signal 92. Since the frequency change amount calculating function obtains the change of the frequency which is required to compensate for the phase difference, the function can be referred to as a so-called phase difference compensation calculating function.

Figure 8:
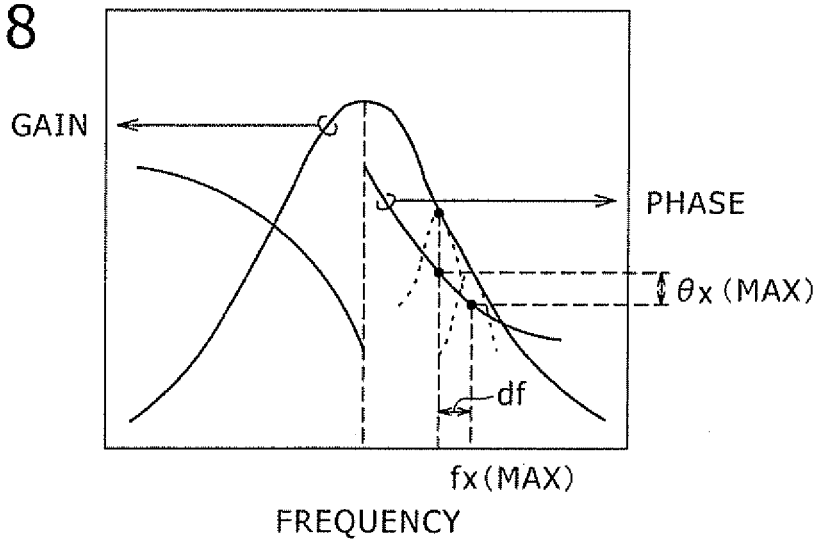
FIG. 8 is an explanatory view of a function of a frequency change amount detection unit in the embodiment according to the present invention.

FIG. 8 is an explanatory view of the function of the frequency change amount detection unit 78. FIG. 8 shows, as the reference transmission characteristic curve, band pass characteristics of a maximum amplitude gain at a resonance frequency in a case where the abscissa indicates the frequency, and the ordinate indicates relative values of the amplitude gain and the phase. Such a reference transmission characteristic curve can be generated by a technology to generate a band pass filter by use of hardware or software. The reference transmission characteristic curve is a conversion curve for converting the change of the phase to the change of the frequency, and the curve itself can be designed based on a degree of a conversion ratio between the phase and the frequency.

When the phase difference compensating calculation is performed by using this reference transmission characteristic curve, first the frequency fx(MAX) and the phase difference θx(MAX) are obtained on this reference transmission characteristic curve. Here, the value is moved as much as the phase difference θx(MAX) along a phase difference characteristic curve to obtain the corresponding frequency change amount df. In this case, the frequency change amount for setting the phase difference θx(MAX) to zero is obtained as df.

The data of the frequency and the phase difference reflects material characteristics corresponding to the hardness of the hard spot 18 inside the biological tissue 16. Among the characteristics, it is considered that the frequency fx(MAX) at which the change of the phase difference becomes largest and the maximum phase difference θx(MAX) especially typically indicate the hardness of the hard spot 18 inside the biological tissue 16 which is a measurement target. Therefore, the frequency change amount df for shifting the maximum phase difference θx(MAX) to zero is calculated, whereby a characteristic value typically indicating the hardness of the hard spot 18 inside the biological tissue 16 can be obtained.

Further contents of the frequency component analysis unit 74, the phase difference calculation unit 76 (frequency phase difference specifying) and the frequency change amount detection unit 78 (phase difference compensating calculation) are disclosed in detail by JP-A-2002-272743.

A hardness converter 80 has a function of converting the frequency change amount df to the hardness of the biological tissue. When the frequency change amount df is converted to the hardness of the biological tissue, a calibration table or the like can be used. The calibration table can be obtained by pressing a reference material, from which a hardness reference can be obtained, against a tip of the contact ball 30 of the probe element 22, and as described in the above procedure, introducing the pulse wave, detecting the reflected wave to execute the frequency component analysis, and obtaining the frequency change at this time.

Figure 9:
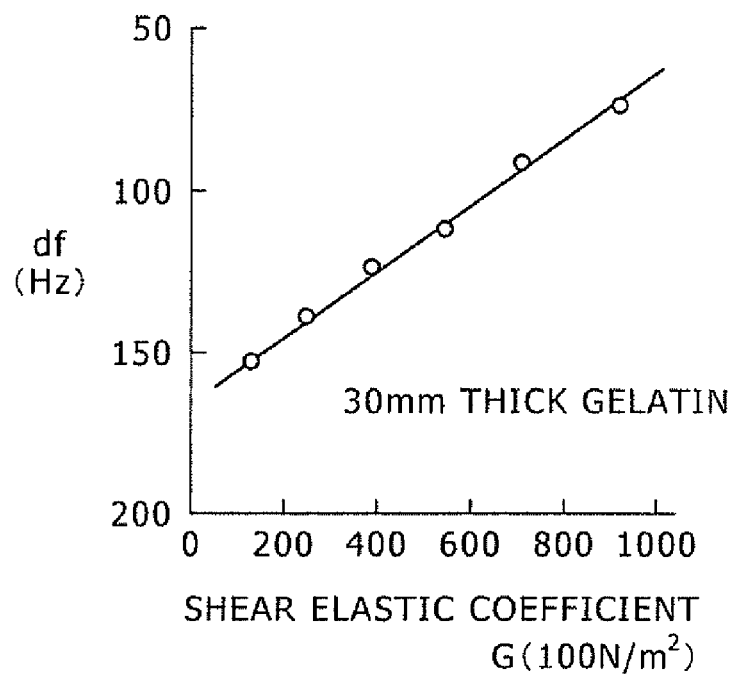
FIG. 9 is a diagram showing an example in which a relation between a shear elastic coefficient to express the hardness and a frequency change amount in the embodiment according to the present invention.

FIG. 9 shows an example in which a relation between a shear elastic coefficient G and the amount df is obtained as the reference of the hardness by use of gelatin having different hardness and a thickness of 30 mm. As shown in FIG. 9, it is seen that there is a clearly linear relation between G indicating the hardness and the frequency change amount df obtained in the procedure described with reference to FIG. 5. The result can be used as a calibration characteristic curve for converting the frequency change amount df to the hardness, or the calibration table.

As described with reference to FIG. 3, an output of the hardness converter 80 is correlated with the address of the probe element 22 and supplied to the data collection unit 84.

Figure 10:
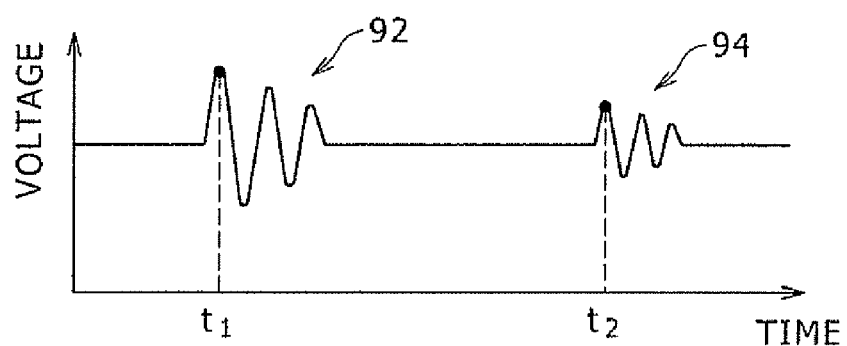
FIG. 10 is a diagram showing a calculation of the measurement depth in the embodiment according to the present invention.

Next, contents of the measurement depth calculation unit 82 will be described. As described with reference to FIG. 4, the measurement depth calculation unit 82 calculates the measurement depth of the hard spot 18 on the basis of the temporal position t1 of the incident wave signal 92 and the temporal position t2 of the reflected wave signal 94 by use of a propagation velocity v of the ultrasonic wave through the biological tissue 16. The temporal positions t1 and t2 of the incident wave signal 92 and the reflected wave signal 94 can be detected by detecting maximum peaks, respectively, as shown in, for example, voltage-time characteristics of FIG. 10.

The maximum peaks can be detected by using an appropriate voltage threshold value, signal differential processing or the like. That is, when appropriate threshold values are set to voltage values which are amplitudes of the incident wave signal 92 and the reflected wave signal 94, only maximum peaks can be selected, respectively. The waveform of the selected maximum peak is subjected to differential processing, and a zero cross point is obtained, whereby the peak detection can be performed. The time when the peak has been detected can be used as the temporal position t1 of the incident wave signal 92 and the temporal position t2 of the reflected wave signal 94.

Figure 11:
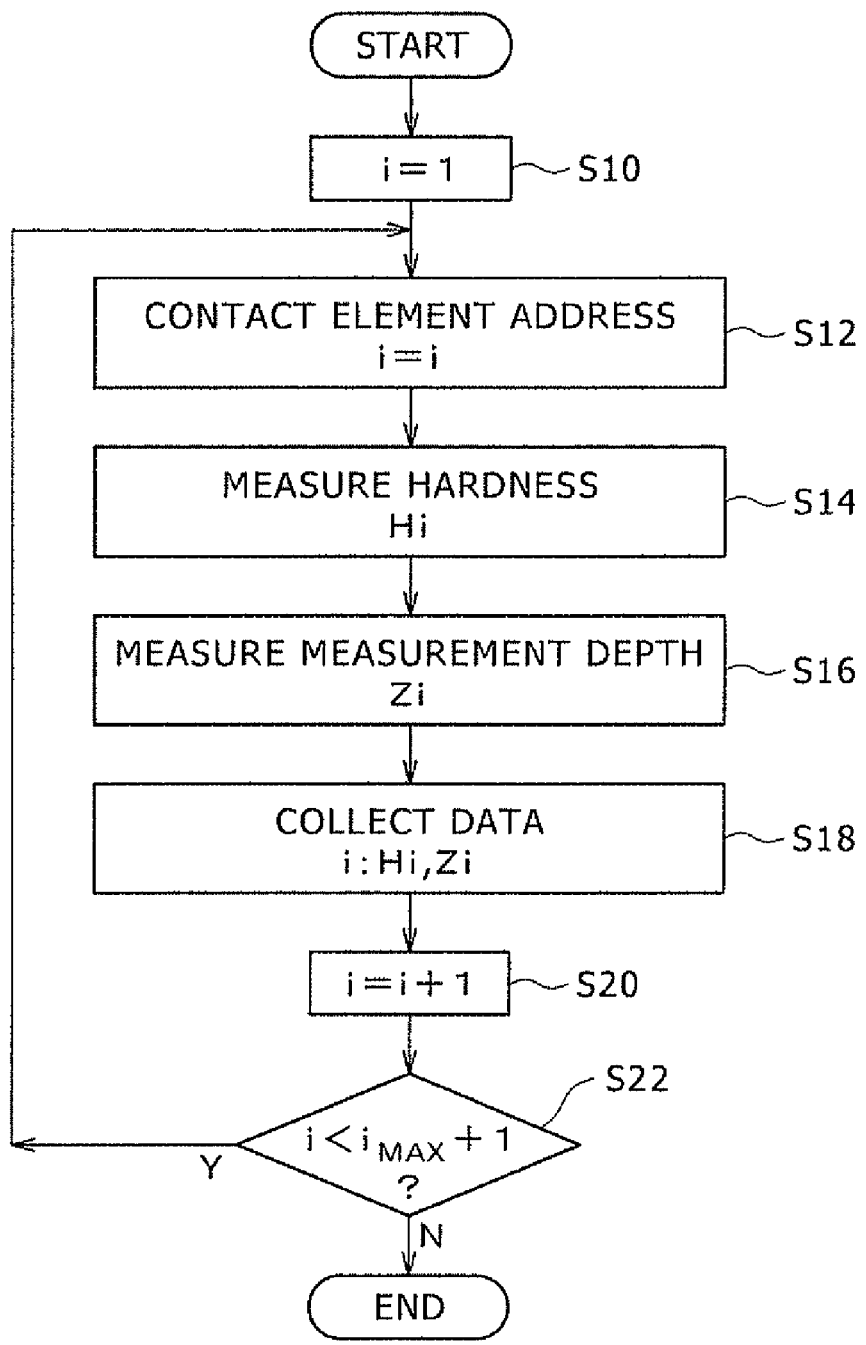
FIG. 11 is a flowchart showing a procedure of data collection for accomplishing three-dimensional display of the hardness in the embodiment according to the present invention.
Figure 12:
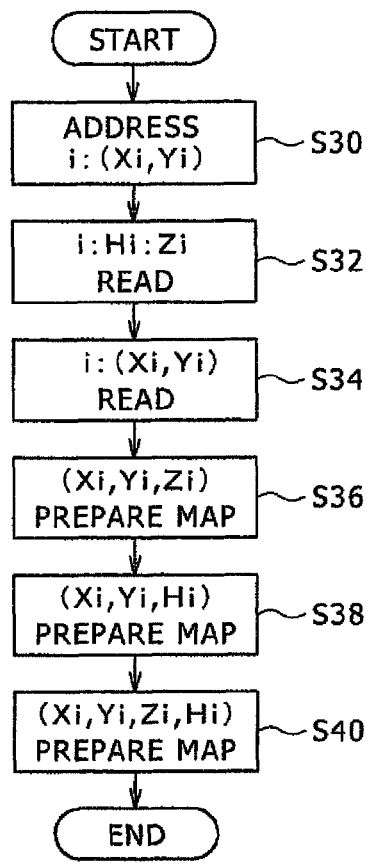
FIG. 12 is a flowchart showing a procedure to accomplish the three-dimensional display of the hardness on the basis of the data collection in the embodiment according to the present invention.

Next, a procedure to specifically obtain the three-dimensional display of the hardness will be described in detail. FIG. 11 and FIG. 12 are flowcharts showing a procedure to perform three-dimensional display. The procedures correspond to processing procedures of the material hardness distribution display program executed by a CPU of the controller 40. FIG. 11 shows a procedure concerned with the hardness calculation unit 70, the measurement depth calculation unit 82, and the data collection unit 84, and FIG. 12 shows a procedure concerned with the display processing unit 86 and the display unit 88.

When the three-dimensional display of the hardness is performed, the probe unit 20 is pressed against the biological tissue 16, and the hardness and the measurement depth of the respective probe elements 22 are successively measured. The successive measurement is performed by using the identification addresses of the probe elements 22. In FIG. 11, when the identification address number of the probe element 22 is i, i is increased in order from 1 to a maximum value of i, i.e., iMAX=37, thereby measuring the hardness and the measurement depth.

That is, i=1 is set as an initial state (S10). In this setting, the switch circuit 50 connects the probe element 22 corresponding to an identification address i=1 to the pulse wave generator 60 (S12). In consequence, the pulse wave is supplied to the oscillator 26 of the probe element 22, and the ultrasonic pulse wave is introduced into the biological tissue 16. Moreover, since the probe element 22 is connected to the hardness calculation unit 70 and the measurement depth calculation unit 82, by the method described with reference to FIG. 4 to FIG. 10, hardness Hi and a measurement depth Zi are measured by use of the incident wave signal 92 and the reflected wave signal 94, respectively (S14 and S16). The measured result is correlated with the identification address i=1, and hardness H1 and measurement depth Z1 are transmitted to and stored in the data collection unit 84.

Next, the number of the identification address i is advanced by 1 (S20), and it is judged whether or not the advanced number exceeds iMAX+1 (S22). When the number does not exceed the value, it is judged that the measurement of the probe element 22 has not completely ended, thereby returning to S12 and repeating the above measurement. In consequence, the hardness and the measurement depth of all the probe elements 22 are successively measured. Then, in the data collection unit 84, the hardness Hi and the measurement depth Zi are correlated with the identification address i and stored in the data collection unit 84.

FIG. 12 shows a procedure to display the three-dimensional distribution of the hardness with respect to the hard spot 18 inside the biological tissue 16, on the basis of the data stored in the data collection unit 84. In the controller 40, a relation between the identification address i of the probe element and a coordinate position (Xi, Yi) of the probe element 22 in a two-dimensional coordinate system is stored beforehand in an appropriate memory with respect to all the probe elements 22 (S30). In the material hardness distribution display system 10, this relation data can be stored by previously inputting the data from an input unit of the controller 40 when the probe unit 20 is set or the like.

Then, to display the three-dimensional hardness distribution, the hardness Hi and the measurement depth Zi are read from the data collection unit 84 using the identification address i of the probe element 22 as a search key (S32). Then, the two-dimensional coordinate position (Xi, Yi) of the identification address i is read from the memory of the controller 40 (S34). In consequence, the coordinate (Xi, Yi) of the two-dimensional coordinate system and the hardness Hi and the measurement depth Zi at the position are correlated and read.

Figure 13:
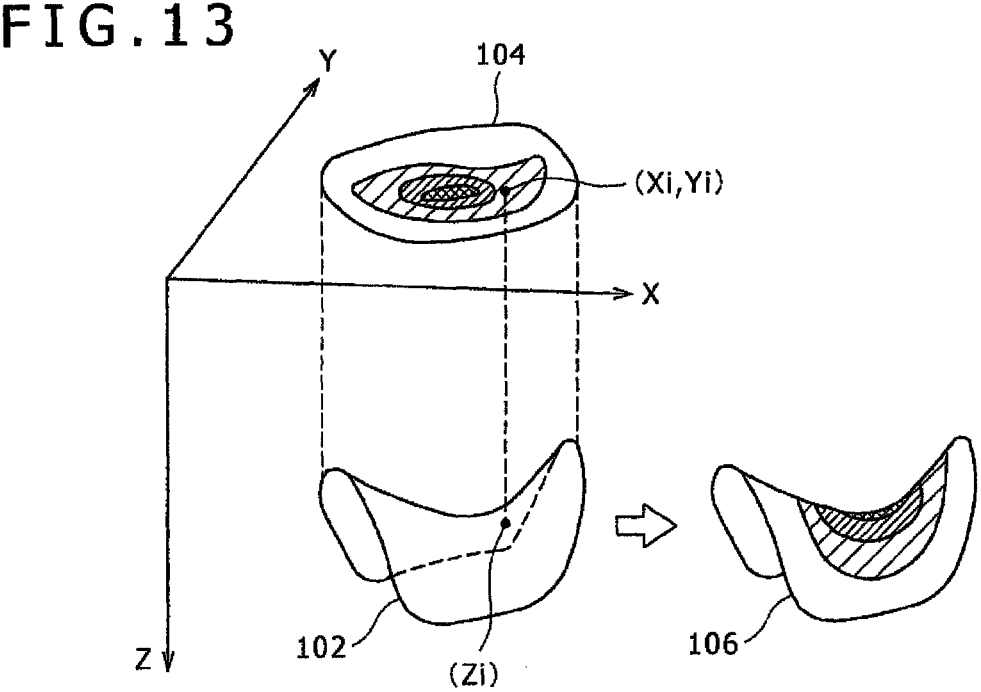
FIG. 13 is an explanatory view of obtaining a measurement depth distribution, a hardness distribution, and a three-dimensional distribution of the hardness in the embodiment according to the present invention.

Next, processing is performed to prepare a map of the distribution of Zi in the two-dimensional coordinate system in order from i=1 to 37 by use of the coordinate (Xi, Yi) of the two-dimensional coordinate system and the data of the measurement depth Zi at the position, thereby displaying the image of the map (S36). This processing prepares the image of the outer shape of the hard spot 18 in the biological tissue 16. FIG. 13 shows a measurement depth distribution 102 obtained by smoothly connecting 37 sets of (Xi, Yi, Zi). This example shows that the distribution of the measurement depth when the ultrasonic pulse is introduced into the biological tissue 16 and reflected has a planar saddle shape.

Next, processing is performed to prepare a map of the distribution of Hi in the two-dimensional coordinate system in order from i=1 to 37 by use of the coordinate (Xi, Yi) of the two-dimensional coordinate system and the data of the hardness Hi at the position, thereby displaying the image of the map (S38). This processing associates the result of the measurement of the hardness of the hard spot 18 inside the biological tissue 16 by each of the probe elements 22 with the position of the probe element 22, to form an image. When a size image of the hardness Hi is formed, it is possible to use, for example, a method of changing color phase, color concentration or the like in accordance with the size of Hi. FIG. 13 shows a hardness distribution 104 where the hardness Hi is shown by a hatching density, and 37 sets of (Xi, Yi, Zi) are represented by a distribution of hatching with different densities.

When the measurement depth distribution 102 in the two-dimensional coordinate system and the hardness distribution 104 in the same two-dimensional coordinate system are obtained in this manner, the coordinate (Xi, Yi) is used as a common coordinate for the two distributions, and superimposed to prepare the map, thereby obtaining the three-dimensional distribution of the hardness (S40). In FIG. 13, a three-dimensional hardness distribution 106 obtained in this manner is shown.

It is to be noted that when the data of the three-dimensional hardness distribution 106 shown in FIG. 13 is appropriately processed, as shown in FIG. 1, the three-dimensional display 100 of the hardness can be performed as the display of the set of the two-dimensional hardness distribution for each measurement depth.

INDUSTRIAL APPLICABILITY

A material hardness distribution display system and a material hardness distribution display method according to the present invention can be utilized to display a hardness distribution of a general material including a biological tissue.

DESCRIPTION OF REFERENCE NUMERALS 10 material hardness distribution display system, 16 biological tissue, 18 hard spot, 20 probe unit, 22 probe element, 24 base portion, 26 oscillator, 28 oscillation detection sensor, 30 contact ball, 32, 34, 42 and 44 signal line, 40 controller, 50 switch circuit, 52 switch, 54 scanning unit, 60 pulse wave generator, 70 hardness calculation unit, 72 amplifier, 74 frequency component analysis unit, 76 phase difference calculation unit, 78 frequency change amount detection unit, 80 hardness converter, 82 measurement depth calculation unit, 84 data collection unit, 86 display processing unit, 88 display unit, 90 generic control unit, 92 incident wave signal, 94 reflected wave signal, 100 and 106 three-dimensional display of hardness, 102 measurement depth distribution, and 104 hardness distribution.

The invention claimed is:

1. A material hardness distribution display system comprising:
an oscillator which introduces a pulse wave into a material to be measured;
an oscillation detection sensor which receives a reflected wave, when the introduced pulse wave is reflected from the material to be measured;
incident wave frequency component analysis means for executing a frequency analysis which breaks down the incident wave into a plurality of sine wave components and cosine wave components, to obtain a spectral distribution of a frequency of each of the sine wave components and a phase obtained from the sine wave component and the cosine wave component at the frequency;
reflected wave frequency component analysis means for executing a frequency analysis which breaks down the reflected wave into a plurality of sine wave components and cosine wave components, to obtain a spectral distribution of a frequency of each of the sine wave components and a phase obtained from the sine wave component and the cosine wave component at the frequency;
frequency phase difference calculation means for comparing the spectral distribution of the incident wave with the spectral distribution of the reflected wave, and calculating, with respect to each of frequencies fx constituting the distributions, a phase difference θx which is a difference between the phase of the incident wave and the phase of the reflected wave at the frequency fx;
hardness calculation means for calculating the hardness of the material to be measured, on the basis of data of a set of the frequency fx and the phase difference θx;
measurement depth calculation means for calculating a measurement depth which is a depth at a position where the hardness has been measured, on the basis of a time of introducing the incident wave and a time of receiving the reflected wave used for the calculation of the hardness; and
display means for correlating and displaying the hardness and the measurement depth.

2. The material hardness distribution display system according to claim 1, wherein the probe elements each including a set of the oscillator and the oscillation detection sensor are two-dimensionally arranged,
the hardness calculation means calculates the hardnesses at positions of the probe elements, respectively, on the basis of the incident waves and the reflected waves by the two-dimensionally arranged probe elements, to obtain a two-dimensional distribution of the hardness,
the measurement depth calculation means calculates measurement depths at the positions of the probe elements, respectively, on the basis of the incident waves and the reflected waves using the two-dimensionally arranged probe elements, to obtain a two-dimensional distribution of the measurement depth, and
the display means correlates the two-dimensional distribution of the hardness and the two-dimensional distribution of the measurement depth, with respect to the material to be measured, to display a three-dimensional hardness distribution.

3. The material hardness distribution display system according to claim 2, further comprising:
storage means for correlating two-dimensional coordinate positions of the probe elements with identification addresses of the probe elements when the probe elements are two-dimensionally arranged, to store the positions,
wherein the hardness calculation means obtains hardnesses at the positions of the probe elements correlated with the identification addresses of the probe elements,
the measurement depth calculation means obtains measurement depths at the positions of the probe elements correlated with the identification addresses of the probe elements,
a reading means reads from the storage means the two-dimensional coordinate position corresponding to the identification address of each of the probe elements,
the display means includes
measurement depth two-dimensional display means for displaying the distribution of the measurement depth in a two-dimensional coordinate system by use of the measurement depth corresponding to the identification address, and
hardness two-dimensional display means for displaying the distribution of the hardness in the two-dimensional coordinate system by use of the hardness at the position of the probe element corresponding to the read identification address,
the display means being configured to superimpose the distribution of the hardness in the two-dimensional coordinate system on the distribution of the measurement depth in the same two-dimensional coordinate system, to display the three-dimensional hardness distribution.

4. The material hardness distribution display system according to claim 1, wherein the hardness calculation means includes:
storage means for storing a previously obtained reference transmission function indicating a relation between an amplitude gain and a phase of the reflected wave with respect to the frequency of the incident wave when the oscillation having an arbitrary frequency is introduced;
a frequency change amount detection unit which inputs the frequency fx and the phase difference θx to obtain df which is a change from the frequency fx when the phase difference θx is set to zero, by use of the reference transmission function; and
hardness conversion means for converting df obtained by the frequency change amount detection unit to the hardness, on the basis of previously obtained hardness-df characteristics.

5. The material hardness distribution display system according to claim 1, wherein the hardness calculation means calculates the hardness of the material to be measured on the basis of a set of a maximum phase difference θx(MAX) and a frequency fx(MAX) corresponding to the maximum phase difference.

6. A material hardness distribution display method comprising:
- an incident wave frequency component analysis step of executing a frequency analysis which breaks down an incident wave introduced as a pulse into a material to be measured by an oscillator into a plurality of sine wave components and cosine wave components, to obtain a spectral distribution of a frequency of each of the sine wave components and a phase obtained from the sine wave component and the cosine wave component at the frequency;
- a reflected wave frequency component analysis step of executing a frequency analysis to break down a reflected wave from the material to be measured which is detected by an oscillation detection sensor, into a plurality of sine wave components and cosine wave components, to obtain a spectral distribution of a frequency of each of the sine wave components and a phase obtained from the sine wave component and the cosine wave component at the frequency;
- a frequency phase difference calculation step of comparing the spectral distribution of the incident wave with the spectral distribution of the reflected wave, to calculate, with respect to each of frequencies fx constituting the distributions, a phase difference θx which is a difference between the phase of the incident wave and the phase of the reflected wave at the frequency fx;
- a hardness calculation step of calculating the hardness of the material to be measured on the basis of data of a set of the frequency fx and the phase difference θx;
- a measurement depth calculation step of calculating a measurement depth which is a depth at a position where the hardness has been measured, on the basis of a time of introducing the incident wave and a time of receiving the reflected wave used for the calculation of the hardness; and
- a display step of correlating and displaying the hardness and the depth.

7. The material hardness distribution display method according to claim 6, wherein
- probe elements each including a set of the oscillator and the oscillation detection sensor are two-dimensionally arranged,
- the hardness calculation step calculates the hardnesses at positions of the probe elements, respectively, on the basis of the incident waves and the reflected waves using the two-dimensionally arranged probe elements, to obtain a two-dimensional distribution of the hardness,
- the measurement depth calculation step calculates measurement depths at the positions of the probe elements, respectively, on the basis of the incident waves and the reflected waves using the two-dimensionally arranged probe elements, to obtain a two-dimensional distribution of the measurement depth, and
- the display step correlates the two-dimensional distribution of the hardness and the two-dimensional distribution of the measurement depth with respect to the material to be measured, to display a three-dimensional hardness distribution.

8. The material hardness distribution display method according to claim 7,
- which uses a storage device which correlates two-dimensional coordinate positions of the probe elements with identification addresses of the probe elements when the probe elements are two-dimensionally arranged and which stores the positions,
- wherein the hardness calculation step obtains hardnesses at the positions of the probe elements correlated with the identification addresses of the probe elements,
- the measurement depth calculation step obtains measurement depths at the positions of the probe elements correlated with the identification addresses of the probe elements,
- a reading step reads from the storage device, the two-dimensional coordinate position corresponding to the identification address of each of the probe elements,
- the display step includes:
- a measurement depth two-dimensional display step of displaying the distribution of the measurement depth in a two-dimensional coordinate system by use of the measurement depth corresponding to the identification address; and
- a hardness two-dimensional display step of displaying the distribution of the hardness in the two-dimensional coordinate system by use of the hardness at the position of the probe element corresponding to the read identification address, and
- the display step superimposes the distribution of the hardness in the two-dimensional coordinate system on the distribution of the measurement depth in the same two-dimensional coordinate system, to display the three-dimensional hardness distribution.

* * * * *